United States Patent [19]

Itoh et al.

[11] Patent Number: 4,957,984

[45] Date of Patent: Sep. 18, 1990

[54] PROCESS FOR PRODUCING HIGHLY WATER ABSORPTIVE POLYMER

[75] Inventors: Kiichi Itoh; Takeshi Shibano; Shuhei Yada; Shinji Tsunoi, all of Yokkaichi, Japan

[73] Assignee: Mitsubishi Petrochemical Company Limited, Tokyo, Japan

[21] Appl. No.: 367,312

[22] Filed: Jun. 16, 1989

[30] Foreign Application Priority Data

Jun. 16, 1988 [JP] Japan ............................. 63-149151
Jul. 22, 1988 [JP] Japan ............................. 63-183365

[51] Int. Cl.$^5$ ............................................. C08F 30/04
[52] U.S. Cl. .................................. 526/240; 526/303.1; 526/319; 526/321; 526/323; 526/323.2; 526/328.5; 526/342
[58] Field of Search .................... 526/323.2, 323, 321, 526/319, 240, 328.5, 303.1, 342

[56] References Cited

U.S. PATENT DOCUMENTS 4,769,427  9/1988  Nowakowsky et al. ............ 526/240
4,833,222  5/1989  Siddall et al. ....................... 526/240

*Primary Examiner*—Joseph L. Schofer
*Assistant Examiner*—Thomas McDonald, Jr.
*Attorney, Agent, or Firm*—Oblon, Spivak, McClelland, Maier & Neustadt

[57] ABSTRACT

A process for producing a highly water adsorptive polymer, which comprises subjecting an aqueous solution of partially neutralized sodium acrylate wherein 20 to 50% or less of the carboxyl group has been neutralized to its sodium salt, the concentration of the partially neutralized sodium acrylate in the aqueous solution being 45 to 80% by weight, to solution polymerization in the presence of a crosslinking agent and optionally not exceeding 20 mol % based on the partially neutralized sodium acrylate of at least one basic vinyl monomer selected from the group consisting of (meth)acrylamide, N,N-dimethyl(meth)acrylamide, dimethylaminoethyl(meth)acrylamide, 2-vinylpyridine, and 4-vinylpyridine with the use of a water soluble radical polymerization initiator.

6 Claims, No Drawings

PROCESS FOR PRODUCING HIGHLY WATER ABSORPTIVE POLYMER

BACKGROUND OF THE INVENTION

1. Field of the Art

This invention is intended to provide a process for producing a highly water absorptive polymer having excellent water absorbing properties with extreme ease and at low cost.

The polymer obtained according to the production process of the present invention can be swelled by absorption of a large amount of water and is insoluble in water, and has a great strength of the swelled gel, and therefore it can be used advantageously for production of various absorbing materials and various materials which are to be used under swelled state with water being absorbed.

2. Prior Art

Materials such as paper, pulp, nonwoven fabric, spongy urethane resins and the like have hitherto been used as water retentive materials for a variety of sanitary goods such as a sanitary napkin, paper diaper and the like and a variety of agricultural materials. However, these materials have a water absorption capacity of no more than 10-50 times their own weight, which causes problems that an extensively increased bulk of the material is required for absorbing or retaining a large amount of water and that water is easily released from the material in which water has been absorbed on pressing it.

There have recently been proposed a variety of highly water absorptive polymer materials and production methods thereof in order to settle the aforementioned problems of the water absorptive materials of this kind. For instance, there have been proposed a graft polymer of starch (Japanese Patent Publication No. 46199/1978, etc.), a denaturated cellulose (Unexamined Published Japanese Patent Application No. 80376/1975, etc.), a crosslinked water soluble polymer (Japanese Patent Publication No. 23462/1968, etc.), a self-crosslinking polymer of an alkali metal salt of acrylic acid (Japanese Patent Publication No. 30710/1979, etc.), crosslinked type polyacrylic acid alkali metal salt (Unexamined Published Japanese Patent Publication No. 71909/1983, Japanese Patent Publication No. 17328/1985).

However, some of these highly water absorptive polymer materials have a number of problems in practical use or production on an industrial scale such that they are still insufficient in amount of water to be absorbed, with the gel strength after water absorption being small, and that the polymer obtained by drying is extremely hard and cannot be easily crushed thereby requiring a great mechanical crushing force. Also, some of those mentioned above employ a large amount of hydrocarbon type solvent, thus involving a serious problem on safety.

A process wherein no hydrocarbon solvents are used may involve polymerizing an aqueous solution of an alkali or ammonium salt of acrylic acid in the absence of a crosslinking agent as disclosed in Unexamined Published Japanese Patent Publication Nos. 58208/1980 and 160302/1983. According to this process, however, it is difficult to obtain a polymer having remarkable water absorbing properties since no crosslinking agent is used and crosslinking takes place due to the self-crosslinking of the acrylate or to obtain a polymer of stable quality from the viewpoint of process operation.

Unexamined Published Japanese Patent Publication Nos. 84304/1980, 108407/1980, 133413/1980, 84632/1981 and 91837/1981 disclose a process for producing highly water absorptive acrylate polymers wherein 50 mol % or more of the carboxyl group has been neutralized with an alkali metal salt in the presence of a polyhydric alcohol and/or a water-soluble and/or water-dispersible surfactant. In accordance with this process, however, the degree of neutralization of the carboxyl group is as high as 50% or more (ordinarily 75% or more) so that, when a sodium salt, for example, is used as the alkali metal salt, the monomer concentration in the aqueous solution can be increased at most up to about 45% by weight and thus enormous energy is required to evaporate a large amount of water contained in the polymer obtained. Furthermore, this process is not so attractive from the process viewpoint since it requires a time as long as 3 to 8 hours for completing polymerization (under such polymerization conditions as in the present invention).

Unexamined Published Japanese Patent Publication No. 71907/1983, on the other hand, discloses a process wherein the monomer concentration can be increased to 55 to 80% by weight with the use of a potassium salt of acrylic acid and the water contained in the product polymer is vaporized by utilizing heat of reaction during polymerization. Nevertheless, this process only affords a polymer having a water absorption capacity not higher than 50 to 60 times its own weight and further tends to involve high cost due to the use of a potassium salt as an alkali metal salt

SUMMARY OF THE INVENTION

The present invention has contributed towards a solution of the above problems and provides a process for producing a highly water absorptive polymer having excellent water absorbing properties by a very simple procedure and yet at low cost.

As a result of extensive research efforts for solving the above problems, we have found that a highly water absorptive polymer endowed with remarkable water absorbing properties can be easily obtained by subjecting an aqueous solution of specific partially neutralized sodium acrylate at a specific concentration to solution polymerization in the presence of a crosslinking agent and optionally a basic vinyl monomer of a specific species and concentration. On the basis of this finding, we have arrived the present invention.

Thus, the process for producing a highly water absorptive polymer according to the present invention comprises subjecting an aqueous solution of partially neutralized sodium acrylate wherein 20 to 50% or less of the carboxyl group has been neutralized to its sodium salt, the concentration of the partially neutralized sodium acrylate in the aqueous solution being 45 to 80% by weight, to solution polymerization in the presence of a crosslinking agent and optionally not exceeding 20 mol % based on the partially neutralized sodium acrylate of at least one basic vinyl monomer selected from the group consisting of (meth)acrylamide, N,N-dimethyl(meth)acrylamide, dimethylaminoethyl(meth)acrylamide, 2-vinylpyridine, and 4-vinylpyridine with the use of a water-soluble radical polymerization initiator.

The process for producing a highly water absorptive polymer according to the present invention has the advantages that, first, a polymer possessing an exceedingly high water absorptive capacity can be obtained by using specific partially neutralized acrylic acid, i.e., partially neutralized acrylic acid wherein 20 to less than 50% of the carboxylic group has been neutralized to its sodium salt, and polymerizing an aqueous solution of the partially neutralized sodium acrylate at a concentration as high as 45 to 80% by weight and optionally in the presence of not exceeding 20 mol % of a specific basic vinyl monomer selected from the group consisting of (meth)acrylamide, N,N-dimethyl(meth)acrylamide, dimethylaminoethyl(meth)acrylamide, 2-vinylpyridine, and 4-vinylpyridine; secondly, drying in a post-treatment can be facilitated and even be omitted in some cases since a substantial part of the water contained in the product polymer can be vaporized by utilizing the heat of polymerization generated abundantly owing to the sodium acrylate in the form of a high-concentration aqueous solution; and thirdly, a high level of safety coupled with excellent process operability can be secured since the process of the present invention does not require the use of any readily flammable hydrocarbon solvent such as hexane or cyclohexane.

It has been quite unexpected that a polymer having a high water absorption capacity can be obtained from sodium acrylate with a degree of partial neutralization of 20 to less than 50%, which falls within such a low degree of neutralization as has not been employed in conventional methods, and further by adding a specific basic monomer as in the process of the present invention. In this respect resides one of the distinguishing features of the present invention.

The highly water absorptive polymer of this invention, by virtue of its remarkable properties, can be used advantageously for production of not only sanitary goods such as sanitary napkins and paper diapers but also various articles for horticulture or agriculture such as soil improvers and water retention agents.

DETAILED DESCRIPTION OF THE INVENTION

Partially neutralized sodium acrylate

Acrylic acid to be used in the present invention is any of those in which 20 to less than 50%, preferably 35 to 45%, of the carboxyl group has been neutralized to its sodium salt.

If the degree of neutralization is below 20%, the water solubility of the partially neutralized sodium acrylate is remarkably increased but the water absorption capacity becomes poor. 50% or higher neutralization is undesirable because the water solubility is drastically reduced (45% or lower) and the water absorption capacity of the product polymer is not materially improved.

While the concentration of the partially neutralized sodium acrylate in the aqueous solution may vary depending upon the degree of neutralization, usually 45 to 80% by weight, preferably 55 to 70% by weight may be employed. If the concentration exceeds 80% by weight, the temperature of the aqueous solution of the partially neutralized sodium acrylate must be raised considerably or the degree of neutralization must be lowered, for example, to below 20%. Conversely, the concentration lower than 45% by weight is unfavorable because the water absorption capacity of the product polymer is not appreciably improved and more energy is required for the subsequent drying procedure due to the higher proportion of water.

In order to neutralize acrylic acid, sodium hydroxide or hydrogencarbonate can be used, sodium hydroxide being especially preferred.

Basic vinyl monomer

The basic vinyl monomer useful herein is a compound having in one molecule thereof a vinyl group copolymerizable with an amino group and/or an amido group. Since an amide is neutral with respect to litmus but reacts with a strong acid to form a salt ("Encyclopaedia Chimica", Vol. 3, Kyoritsu Shuppan, Japan), amide monomers are herein classified as basic monomers.

More specifically, the basic vinyl monomer is at least one selected from the group consisting of (meth)acrylamide, N,N-dimethyl(meth)acrylamide, dimethylaminoethyl(meth)acrylamide, 2-vinylpyridine, and 4-vinylpyridine.

The term "(meth)acrylamide" as used herein refers either to acrylamide or to methacrylamide.

In the "dimethylaminoethyl(meth)acrylamide", one (usually and typically) or two dimethylamino groups may be bound to the N in the (meth)acrylamide.

Among the above enumerated monomers, (meth)acrylamide and vinylpyridine, inter alia, 2-vinylpyridine, are preferred for use in the present invention.

These basic vinyl monomers are used in an amount of generally 20 mol % or less of the partially neutralized acrylic acid, preferably 10 mol % or less. The amount in excess of 20 mol % is undesirable because the water absorption capacity of the product polymer is notably reduced.

Crosslinking agent

The crosslinking agent to be used in the process of the present invention is one which has two or more double bonds in the molecule and is copolymerizable with the partially neutralized sodium acrylate, or one which has two or more functional groups in the molecule that can be reacted with the functional groups in the partially neutralized sodium acrylate such as carboxylic groups during polymerization or upon the subsequent drying. Any compound as mentioned above may be used provided it exhibits water-solubility to some extent.

Examples of the former crosslinking agents may include ethylene glycol di(meth)acrylate, diethylene glycol di(meth)acrylate, polyethylene glycol di(meth)acrylate, propylene glycol di(meth)acrylate, polypropylene glycol di(meth)acrylate, glycerine tri(meth)acrylate, N,N'-methylenebis(meth)acrylamide, diallyl phthalate, diallyl maleate, diallyl terephthalate, triallyl cyanurate, triallyl isocyanurate and triallyl phosphate. The term "(meth)acrylate" herein refers either to acrylate or to methacrylate.

Examples of the latter crosslinking agents may include ethylene glycol diglycidyl ether, polyethylene glycol diglycidyl ether, di- or polyglycidyl ethers of aliphatic polyvalent alcohols.

Further, those compounds which possess both the functions of the former and the latter such as N-methylolacrylamide and glycidyl methacrylate may also be used in the process according to the present invention.

Among the crosslinking agents mentioned above, those having two or more double bonds in the molecule and copolymerizable with the partially neutralized sodium acrylate are preferred.

Specific examples of the preferred crosslinking agents are N,N'-methylenebisacrylamide, N,N'-methylenebismethacrylamide, ethylene glycol diacrylate, ethylene glycol dimethacrylate, diethylene glycol diacrylate, diethylene glycol dimethacrylate, polyethylene glycol diacrylate and polyethylene glycol dimethacrylate.

The crosslinking agents may be used alone or in a mixture of two or more of them.

The amount of the crosslinking agent used is 0.001 to 10% by weight, preferably 0.01 to 2% by weight based on the partially neutralized sodium acrylate. At a level less than 0.001% by weight, while the water absorption capacity of the resulting polymer may be greater, the gel strength of the polymer swelled with water will become smaller. On the other hand, at a level exceeding 10% by weight, while the gel strength can be remarkably enhanced, the water absorption capacity of the polymer becomes too low for practical use.

Water soluble radical polymerization initiator

The water soluble radical polymerization initiator used in this invention is one well known in the art of polymer chemistry. There may be mentioned specifically inorganic or organic peroxides such as persulfates (ammonium salts, alkali metal salts, particularly potassium salts, or the like), hydrogen peroxide, di-tert-butyl peroxide, acetyl peroxide and the like. In addition to these peroxides, it is also possible to use such a radical polymerization initiator as an azo compound or the like, for example 2,2'-azobis(2-amidinopropane) dihydrochloride, 2,2'-azobis(N,N'-dimethyleneisobutylamidine) dihydrochloride and 4,4'-azobis(4-cyano) valeric acid, providing that water solubility in a certain level can be obtained.

The polymerization is initiated by the decomposition of the radical polymerization initiator. Well known as a conventional means for decomposing the initiator is heating. Promotion of the decomposition of the polymerization initiator by means of a chemical substance is also well known in the art. When the polymerization initiator is a peroxide, a promoter of the decomposition thereof is a reducing compound (which is water soluble in this invention) such as an acidic sulfite, ascorbic acid and an amine for a persulfate, and a polymerization initiator comprising a combination of a peroxide and a reducing compound is well known in the art of polymer chemistry as "redox initiator". Thus, the term "polymerization initiator" herein used also involves initiator combined with such decomposition promoting substances, particularly redox initiators.

The amount of such polymerization initiator used is generally 0.001 to 10% by weight, preferably 0.1 to 5% by weight, based on the partially neutralized sodium acrylate.

Polymerization

As has been set forth hereinbefore, the process for producing a highly water absorptive polymer according to the present invention comprises polymerizing an aqueous solution of partially neutralized sodium acrylate wherein 20 to 50% or less, preferably 35 to 45% or less, of the carboxyl group has been neutralized to its sodium salt, the concentration of the partially neutralized sodium acrylate in the aqueous solution being 45 to 80% by weight, preferably 55 to 70% by weight, in the presence of a crosslinking agent and optionally a basic vinyl monomer with the use of a water-soluble radical polymerization initiator.

The partially neutralized sodium acrylate, crosslinking agent, basic vinyl monomer, and water-soluble radical polymerization initiator may be added in any order and the polymerization may be carried out in any manner so long as the desired objects of the present invention can be accomplished.

Exemplary methods are: (a) a method which involves dissolving in advance a radical polymerization initiator in an aqueous solution of partially neutralized sodium acrylate comprising a crosslinking agent and a basic vinyl monomer dissolved therein and then heating the aqueous solution to cause polymerization; (b) a method which involves heating in advance an aqueous solution of partially neutralized sodium acrylate comprising a crosslinking agent and a basic vinyl monomer dissolved therein and adding a radical polymerization initiator to cause polymerization without heating externally; and (c) a method in which a redox polymerization initiator is used as a radical polymerization initiator and which involves dissolving either one of a peroxide and a reducing agent in an aqueous solution of partially neutralized sodium acrylate comprising a crosslinking agent and a basic vinyl monomer dissolved therein and then adding the other to cause polymerization. The polymerization by these methods can be carried out in an inert gas atmosphere, such as nitrogen or argon, or in the air.

The polymerization can be conducted of course in a conventional vessel-type reactor for batchwise reactions and also in a belt-conveyor-type reactor. In the present invention wherein the concentration of the partially neutralized sodium acrylate in the aqueous solution is extremely high, polymerization is preferably conducted in the belt-conveyor-type reactor whereby the water contained in the product polymer is vaporized at the same time with the polymerization by heat of polymerization.

EXAMPLE 1

In a 100 cc conical flask, 15.46 g of 48.5% aqueous solution of sodium hydroxide was charged and 7.04 g of water was added thereto. Separately, 30 g of acrylic acid was charged in a 200 cc conical flask, and 100 cc of the aqueous solution of sodium hydroxide prepared above was gradually added under ice-cooling to neutralize the acrylic acid. The neutralization degree was 45%, and the concentration of the partially neutralized sodium acrylate in the aqueous solution was 65% by weight.

Next, 0.0085 g of N,N'-methylenebisacrylamide as a crosslinking agent was added to the aqueous solution of partially neutralized sodium acrylate and dissolved therein, and the temperature of the solution was maintained at 70° C.

Next, 0.1 g of 2,2'-azobis(2-amidinopropane) dihydrochloride as a polymerization initiator, which was dissolved in 2 g of water, was added to the aqueous solution of partially neutralized sodium acrylate, and immediately thereafter the mixture was fed onto a moving endless belt to a thickness of about 5 mm.

Polymerization started about 10 seconds after the feed of the mixture, proceeded while bubbling and vaporizing water, and finished within about 20 seconds from the feed of the mixture. The polymer thus obtained was nearly in a dry state. This polymer was dried at 80° C. under reduced pressure and then crushed to provide a powdery polymer.

EXAMPLE 2

The procedure of Example 1 was repeated except for using as a polymerization initiator 0.05 g of potassium persulfate dissolved in 2 g of water in placed of 2,2'-azobis(2-amidinopropane) dihydrochloride.

Polymerization started about 1 minute after the feed of the mixture, proceeded while bubbling and vaporizing water, and finished within about 3 minutes from the feed of the mixture. The polymer thus obtained was nearly in a dry state and exhibited a porous appearance due to the vaporization of water. This polymer was dried at 80° C. under reduced pressure and then crushed to provide a powdery polymer.

EXAMPLE 3

52.5 g of an aqueous solution of partially neutralized sodium acrylate (neutralization degree: 45%, concentration: 65% by weight) was prepared in the same manner as in Example 1. To this solution was added 0.0085 g of N,N'-methylenebisacrylamide as a crosslinking agent and dissolved therein, and then 1.60 g of 31% aqueous solution of hydrogen peroxide was added and the temperature of the aqueous solution was maintained at 40° C.

Next, 0.2 g of L-ascorbic acid dissolved in 2 g of water was added to and mixed with the above aqueous solution, and immediately thereafter the mixture was fed onto a moving endless belt to a thickness of about 5 mm.

Polymerization started about 5 seconds after the feed of the mixture, proceeded while bubbling and rapidly vaporizing water, and finished within about 10 seconds after the feed of the mixture.

The polymer thus obtained was nearly in a dry state. This polymer was dried at 80° C. under reduced pressure and then crushed to provide a powdery polymer.

EXAMPLE 4

The procedure of Example 3 was repeated except for using as a crosslinking agent 0.25 g of polyethylene glycol (molecular weight: 600) diacrylate in place of N,N'-methylenebisacrylamide.

Polymerization started about 3 seconds after the feed of the mixture, proceeded while bubbling and rapidly vaporizing water, and finished within about 10 seconds from the feed of the mixture.

The polymer thus obtained was dried at 80° C. under reduced pressure and then crushed to provide a powdery polymer.

Comparative Example 1

In a 100 cc conical flask, 25.67 g of 48.5% aqueous solution of sodium hydroxide was charged and 26.26 g of water was added thereto. Separately, 30 g of acrylic acid was charged in a 200 cc conical flask, and 100 cc of the aqueous solution of sodium hydroxide prepared above was gradually added under ice-cooling to neutralize the acrylic acid. The neutralization degree was 75%, and the concentration of the partially neutralized sodium acrylate in the aqueous solution was 45% by weight.

Next, 0.0085 g of N,N'-methylenebisacrylamide as a crosslinking agent was added to the aqueous solution of partially neutralized sodium acrylate and dissolved therein, and the temperature of the solution was maintained at 70° C.

Next, 0.1 g of 2,2'-azobis(2-amidinopropane) dihydrochloride as a polymerization initiator, which was dissolved in 2 g of water, was added to the aqueous solution of partially neutralized sodium acrylate, and immediately thereafter the mixture was fed onto a moving endless belt to a thickness of about 5 mm.

Polymerization started about 30 seconds after the feed of the mixture, proceeded while bubbling and gradually vaporizing water, and finished within about 3 minutes from the feed of the mixture. The polymer thus obtained was a sticky, rubber-like gel. This polymer was dried at 80° C. under reduced pressure and then crushed to provide a powdery polymer.

Comparative Example 2

81.93 g of an aqueous solution of partially neutralized sodium acrylate (neutralization degree: 75%, concentration: 45% by weight) was prepared in the same manner as in Comparative Example 1. To this solution was added 0.0085 g of N,N'-methylenebisacrylamide as a crosslinking agent and dissolved therein, and then 1.60 g of 31% aqueous solution of hydrogen peroxide was added and the temperature of the aqueous solution was maintained at 40° C.

Next, 0.2 g of L-ascorbic acid dissolved in 2 g of water was added to and mixed with the above aqueous solution, and immediately thereafter the mixture was fed onto a moving endless belt to a thickness of about 5 mm.

Polymerization started about 10 seconds after the feed of the mixture, proceeded while bubbling and gradually vaporizing water, and finished within about 1 minute after the feed of the mixture.

The polymer thus obtained was a sticky, rubber-like gel. This polymer was dried at 80° C. under reduced pressure and then crushed to provide a powdery polymer.

For the polymers obtained in the above Examples and Comparative Examples, the following test was conducted to evaluate water absorbing ability. The results are shown in Table 1.

Water absorbing ability

About 2 g of the polymer and about 500 g of a saline solution having a concentration of about 0.9% by weight were respectively weighed and charged in one liter-beaker. After stirring, the beaker was left standing for 5 hours to have the polymer sufficiently swelled with the saline solution. Next, the beaker content was sufficiently drained through a 100 mesh filter, and the amount of the swelled gel was measured and the water absorbing ability was calculated according to the following formula:

$$\text{Water absorbing ability (g/g resin)} = \frac{\text{Weight of swelled gel(g)}}{\text{Charged amount of polymer(g)}}$$

TABLE 1

| Example No. | Water absorbing ability (g/g resin) |
|---|---|
| Example 1 | 69.5 |
| Example 2 | 65.5 |
| Example 3 | 72.1 |
| Example 4 | 69.8 |
| Comp. Example 1 | 48.2 |

TABLE 1-continued

| Example No. | Water absorbing ability (g/g resin) |
| --- | --- |
| Comp. Example 2 | 45.2 |

EXAMPLE 5

In a 100 cc conical flask, 15.46 g of 48.5% aqueous solution of sodium hydroxide was charged and 7.04 g of water was added thereto. Separately, 30 g of acrylic acid was charged in a 200 cc conical flask, and 100 cc of the aqueous solution of sodium hydroxide prepared above was gradually added under ice-cooling to neutralize the acrylic acid. The neutralization degree was 45%, and the concentration of the partially neutralized sodium acrylate in the aqueous solution was 65% by weight.

Next, 0.0085 g of N,N'-methylenebisacrylamide as a crosslinking agent and 0.25 g of 2-vinylpyridine as a basic vinyl monomer were added to the aqueous solution of partially neutralized sodium acrylate and dissolved therein, and the temperature of the solution was maintained at 70° C.

Next, 0.1 g of 2,2'-azobis(2-amidinopropane) dihydrochloride as a polymerization initiator, which was dissolved in 2 g of water, was added to the aqueous solution of partially neutralized sodium acrylate, and immediately thereafter the mixture was fed onto a moving endless belt to a thickness of about 5 mm.

Polymerization started about 20 seconds after the feed of the mixture, proceeded while bubbling and vaporizing water, and finished within about 30 seconds from the feed of the mixture. The polymer thus obtained was nearly in a dry state. This polymer was dried at 80° C. under reduced pressure and then crushed to provide a powdery polymer.

EXAMPLE 6

The procedure of Example 5 was repeated except for using as a polymerization initiator 0.05 g of potassium persulfate dissolved in 2 g of water in placed of 2,2'-azobis(2-amidinopropane) dihydrochloride and 2 g of acrylamide as a basic vinyl monomer in place of 2-vinylpyridine.

Polymerization started about 1.5 minute after the feed of the mixture, proceeded while bubbling and vaporizing water, and finished within about 3 minutes from the feed of the mixture. The polymer thus obtained was nearly in a dry state and exhibited a porous appearance due to the vaporization of water. This polymer was dried at 80° C. under reduced pressure and then crushed to provide a powdery polymer.

EXAMPLE 7

52.5 g of an aqueous solution of partially neutralized sodium acrylate (neutralization degree: 45%, concentration: 65% by weight) was prepared in the same manner as in Example 5. To this solution were added 0.0085 g of N,N'-methylenebisacrylamide as a crosslinking agent and 0.25 g of 2-vinylpyridine as a basic vinyl monomer and dissolved therein, and then 1.60 g of 31% aqueous solution of hydrogen peroxide was added and the temperature of the aqueous solution was maintained at 40° C.

Next, 0.2 g of L-ascorbic acid dissolved in 2 g of water was added to and mixed with the above aqueous solution, and immediately thereafter the mixture was fed onto a moving endless belt to a thickness of about 5 mm.

Polymerization started about 10 seconds after the feed of the mixture, proceeded while bubbling and rapidly vaporizing water, and finished within about 15 seconds after the feed of the mixture.

The polymer thus obtained was nearly in a dry state. This polymer was dried at 80° C. under reduced pressure and then crushed to provide a powdery polymer.

EXAMPLE 8

The procedure of Example 7 was repeated except for using as a crosslinking agent 0.25 g of polyethylene glycol (molecular weight: 600) diacrylate in place of N,N'-methylenebisacrylamide and 3 g of N,N-dimethylaminoethylmethacrylamide as a basic vinyl monomer in place of 2-vinylpyridine.

Polymerization started about 5 seconds after the feed of the mixture, proceeded while bubbling and rapidly vaporizing water, and finished within about 15 seconds from the feed of the mixture.

The polymer thus obtained was dried at 80° C. under reduced pressure and then crushed to provide a powdery polymer.

For each of the polymers obtained in Examples 5–8, the water absorbing ability was determined in the same way as set forth above. The results are shown in Table 2 below.

TABLE 2

| Example No. | Water absorbing ability (g/g resin) |
| --- | --- |
| Example 5 | 85.1 |
| Example 6 | 88.2 |
| Example 7 | 90.3 |
| Example 8 | 83.1 |

What is claimed is:

1. A process for producing a highly water absorptive polymer, which comprises subjecting an aqueous solution of partially neutralized sodium acrylate wherein 20 to 45% of the carboxyl group has been neutralized to its sodium salt, the concentration of said partially neutralized sodium acrylate in the aqueous solution being 55 to 80% by weight, to solution polymerization in the presence of a crosslinking agent and 0–20 mol % based on said partially neutralized sodium acrylate of at least one basic vinyl monomer selected from the group consisting of (meth)acrylamide, N,N-dimethyl(meth)acrylamide, dimethylaminoethyl(meth)acrylamide, 2-vinylpyridine, and 4-vinylpyridine with the use of a water soluble radical polymerization initiator.

2. The process according to claim 1, wherein the basic vinyl monomer is 2-vinylpyridine.

3. The process according to claim 1, wherein the crosslinking agent is selected from the group consisting of N,N'-methylenebisacrylamide, N,N'-methylenebismethacrylamide, ethylene glycol diacrylate, ethylene glycol dimethacrylate, diethylene glycol diacrylate, diethylene glycol dimethacrylate, polyethylene glycol diacrylate and polyethylene glycol dimethacrylate.

4. The process according to claim 1, wherein the amount of the crosslinking agent used is 0.001 to 10% by weight based on the partially neutralized sodium acrylate.

5. The process according to claim 1, wherein the water soluble radical polymerization initiator is a redox initiator.

6. The process according to claim 1, wherein the amount of the water soluble radical polymerization initiator used is 0.001 to 10% by weight based on the partially neutralized sodium acrylate.

* * * * *